US012678389B1

(12) United States Patent (10) Patent No.: US 12,678,389 B1
Thornhill (45) Date of Patent: Jul. 14, 2026

(54) METHODS OF TREATING DOG DENTAL HEALTH AND RELATED COMPOSITIONS AND RELATED KITS

(71) Applicant: Life's Abundance, Jupiter, FL (US)

(72) Inventor: Lester Thornhill, Jupiter, FL (US)

(73) Assignee: Life's Abundance, Jupiter, FL (US)

( * ) Notice: Subject to any disclaimer, the term of this patent is extended or adjusted under 35 U.S.C. 154(b) by 0 days.

(21) Appl. No.: 19/080,539

(22) Filed: Mar. 14, 2025

(51) Int. Cl.
| | |
|---|---|
| A61K 8/66 | (2006.01) |
| A61K 8/19 | (2006.01) |
| A61K 8/365 | (2006.01) |
| A61K 8/67 | (2006.01) |
| A61K 8/9789 | (2017.01) |
| A61K 8/9794 | (2017.01) |
| A61K 8/98 | (2006.01) |
| A61Q 11/00 | (2006.01) |

(52) U.S. Cl.
CPC .................. *A61K 8/66* (2013.01); *A61K 8/19* (2013.01); *A61K 8/365* (2013.01); *A61K 8/676* (2013.01); *A61K 8/9789* (2017.08); *A61K 8/9794* (2017.08); *A61K 8/988* (2013.01); *A61Q 11/00* (2013.01); *A61K 2800/87* (2013.01); *C12Y 101/03004* (2013.01)

(58) Field of Classification Search
CPC ...... A61K 8/66; A61K 8/9794; A61K 8/9789; A61K 8/19; A61K 8/365; A61K 8/676; A61K 8/988; A61Q 11/00
See application file for complete search history.

(56) References Cited

U.S. PATENT DOCUMENTS

| | | |
|---|---|---|
| 9,968,548 B2 | 5/2018 | DuBourdieu et al. |
| 10,835,485 B2 | 11/2020 | Pompejus |

| | | |
|---|---|---|
| 2007/0140990 A1 | 6/2007 | Fetissova et al. |
| 2013/0266521 A1 | 10/2013 | Fetissova et al. |
| 2013/0280183 A1 | 10/2013 | Salazar Navarrete et al. |
| 2016/0128932 A1 | 5/2016 | DuBourdieu et al. |
| 2018/0028843 A1 | 2/2018 | Albert |
| 2022/0000907 A1* | 1/2022 | Rosov .................... A61Q 11/00 |

FOREIGN PATENT DOCUMENTS

| | | | | |
|---|---|---|---|---|
| BR | 102017019843 A2 * | 4/2019 | .............. | A61K 8/97 |
| EP | 1973515 A1 | 10/2008 | | |
| EP | 2808009 A1 | 12/2014 | | |
| WO | WO-2005063184 A1 * | 7/2005 | ........... | A61K 8/9794 |

OTHER PUBLICATIONS

Vallasenor, Y., What Is Yucca Schidigera? And Is It Safe for Dogs? We Asked a Vet., The Dog's Life, Sep. 11, 2022. (Year: 2022).*

* cited by examiner

*Primary Examiner* — Lezah Roberts
(74) *Attorney, Agent, or Firm* — GREENBERG TRAURIG, LLP

(57) ABSTRACT

Methods of treating dog dental health and related compositions and related methods are provided. The method of treating dog health comprises obtaining a composition. The composition comprises active ingredients and at least one supporting ingredient. The active ingredients comprises a *Yucca schidigera* extract, a propolis extract, and a glucose oxidase. The glucose oxidase is present in a sufficient amount, so when digested by a dog, generates a plurality of hydrogen peroxide molecules to enhance antimicrobial anti-inflammatory properties of the active ingredients. The at least one supporting ingredient comprises a radish root ferment filtrate. The at least one supporting ingredient is present in a sufficient amount to maintain a potency of the active ingredients. The method comprises administering to a dog between about 1 to 20 drops of the composition to a tap water to improve a saliva score by at least 50% as detected by Active Matrix Metalloproteinase-8 (aMMP-8).

14 Claims, 4 Drawing Sheets

METHODS OF TREATING DOG DENTAL HEALTH AND RELATED COMPOSITIONS AND RELATED KITS

FIELD

The present disclosure relates to methods of treating dog dental health and related compositions and related kits.

BACKGROUND

Dental disease represents one of the most common health issues in companion pets.

SUMMARY

Some embodiments relate to a method of treating dog dental health. In some embodiments, the method comprises obtaining a composition. In some embodiments, the composition comprises active ingredients. In some embodiments, the active ingredients comprises a *Yucca schidigera* extract, a propolis extract, and a glucose oxidase. In some embodiments, the glucose oxidase is present in a sufficient amount, so when digested by a dog, generates a plurality of hydrogen peroxide molecules to enhance antimicrobial anti-inflammatory properties of the active ingredients. In some embodiments, the composition comprises at least one supporting ingredient. In some embodiments, the at least one supporting ingredient comprises a radish root ferment filtrate. In some embodiments, the at least one supporting ingredient is present in a sufficient amount, so when digested by a dog, the at least one supporting ingredient maintains a potency of the active ingredient. In some embodiments, the method comprises administering to a dog between about 1 to 20 drops of the composition to a tap water to improve a saliva score by at least 50% as detected by Active Matrix Metalloproteinase-8 (aMMP-8).

Some embodiments relate to a composition. In some embodiments, the composition comprises active ingredients. In some embodiments, the active ingredients comprises a *Yucca schidigera* extract, a propolis extract, and a glucose oxidase. In some embodiments, the glucose oxidase is present in a sufficient amount, so when digested by a dog, generates a plurality of hydrogen peroxide molecules to enhance antimicrobial anti-inflammatory properties of the active ingredients. In some embodiments, the composition comprises at least one supporting ingredient. In some embodiments, the at least one supporting ingredient comprises a radish root ferment filtrate. In some embodiments, the at least one supporting ingredient is present in a sufficient amount, so when digested by a dog, the at least one supporting ingredient maintains a potency of the active ingredients.

Some embodiments relate to a kit. In some embodiments, the kit comprises a composition. In some embodiments, the composition comprises active ingredients. In some embodiments, the active ingredients comprises a *Yucca schidigera* extract, a propolis extract, and a glucose oxidase. In some embodiments, the glucose oxidase is present in a sufficient amount, so when digested by a dog, generates a plurality of hydrogen peroxide molecules to enhance antimicrobial anti-inflammatory properties of the active ingredients. In some embodiments, the composition comprises at least one supporting ingredient. In some embodiments, the at least one supporting ingredient comprises a radish root ferment filtrate. In some embodiments, the at least one supporting ingredient is present in a sufficient amount, so when digested by a dog, the at least one supporting ingredient maintains a potency of the active ingredients. In some embodiments, the kit comprises a storage container. In some embodiments, the storage container comprises an amber glass. In some embodiments, the storage container comprises a label. In some embodiments, the label covers at least 80% of the storage container. In some embodiments, the storage container contains the composition to stabilize at least one of the active ingredients and the at least one supporting ingredient, or any combination thereof. In some embodiments, the storage container provides a light barrier to the composition.

DRAWINGS

DETAILED DESCRIPTION

Among those benefits and improvements that have been disclosed, other objects and advantages of this disclosure will become apparent from the following description taken in conjunction with the accompanying figures. Detailed embodiments of the present disclosure are disclosed herein; however, it is to be understood that the disclosed embodiments are merely illustrative of the disclosure that may be embodied in various forms. In addition, each of the examples given regarding the various embodiments of the disclosure which are intended to be illustrative, and not restrictive.

Any prior patents and publications referenced herein are incorporated by reference in their entireties.

Throughout the specification and claims, the following terms take the meanings explicitly associated herein, unless the context clearly dictates otherwise. The phrases "in one embodiment," "in an embodiment," and "in some embodiments" as used herein do not necessarily refer to the same embodiment(s), though it may. Furthermore, the phrases "in another embodiment" and "in some other embodiments" as used herein do not necessarily refer to a different embodiment, although it may. All embodiments of the disclosure are intended to be combinable without departing from the scope or spirit of the disclosure.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

Dental health is a cornerstone indicator of a companion pet wellness. Poor dental health such as poor oral hygiene in companion pets can cause gum disease, tooth loss, and systemic problems affecting the heart, liver, and kidneys. Less than 2% of pet owners brush their companion pets' teeth regularly which leads to complex dental procedures, if not treated. The methods and related compositions and related kits overcome the challenges associated with not maintaining regular dental hygiene on companion pets.

Figure 1:
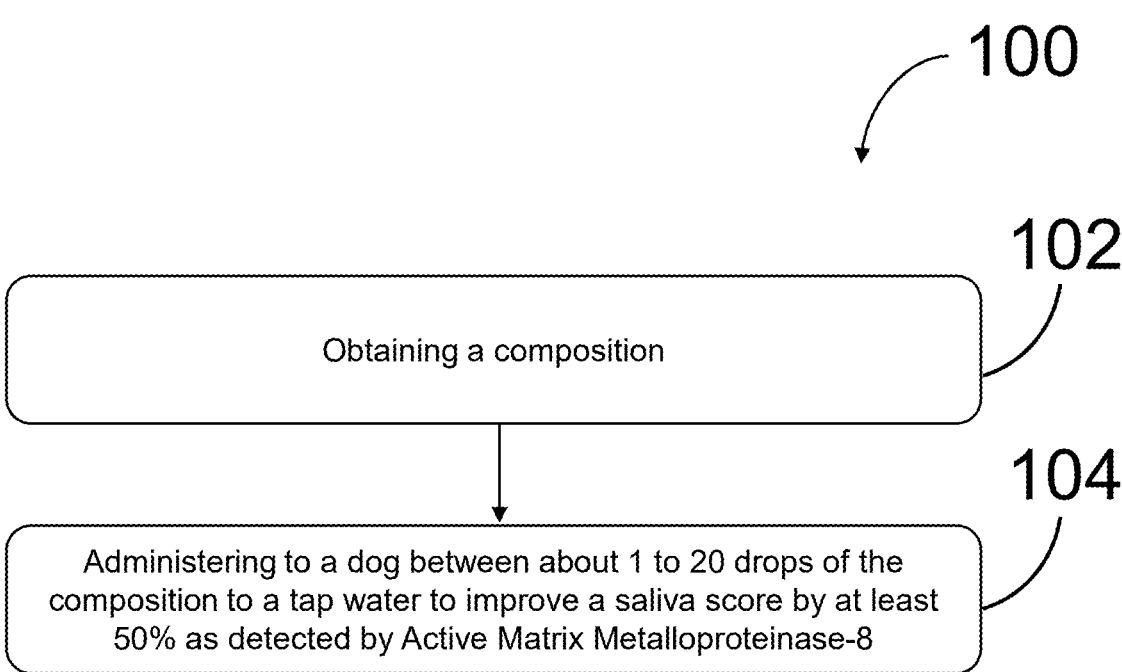
FIG. 1 is a flowchart of a method of treating dog dental health, according to some embodiments.

FIG. 1 is a flowchart of a method 100, according to some embodiments. As shown in FIG. 1, the method 100 may comprise one or more of the following steps: obtaining 102 a composition and administering 104 to a dog between about 1 to 20 drops of the composition to a tap water to improve a saliva score by at least 50% as detected by Active Matrix Metalloproteinase-8 (aMMP-8).

At step 102, in some embodiments, the method comprises obtaining a composition. In some embodiments, the composition can comprise active ingredients and at least one supporting ingredient. In some embodiments, the composition can be used to prevent or treat dental disease. In some embodiments, the composition can reduce plaque and tartar buildup, improve gum health, freshen breath, support for overall oral hygiene, and improve systemic health due to better oral care.

In some embodiments, the composition can enhance efficacy. In some embodiments, the active ingredients in the composition can provide a profile for improved plaque and tartar control compared to traditional compositions. In some embodiments, the composition can be palatable. Unlike traditional compositions, in some embodiments, the composition can be sensitive to pets' sensitive to strong tastes. In some embodiments, the composition can comprise natural ingredients. In some embodiments, the composition can be easy to use. In some embodiments, the composition can integrate into daily hygiene routines.

In some embodiments, the active ingredients in the composition can comprise a *Yucca schidigera* extract, a propolis extract, and a glucose oxidase.

In some embodiments, the active ingredient in the composition can comprise a *Yucca schidigera* extract. In some embodiments, the *Yucca schidigera* extract can be derived from a Mojave *Yucca* plant. In some embodiments, the *Yucca schidigera* can be a liquid. In some embodiments, the *Yucca schidigera* can be a powder.

In some embodiments, the *Yucca schidigera* extract can be food grade. In some embodiments, the *Yucca schidigera* contains 50% water-soluble *Yucca* extract solids. In some embodiments, the *Yucca schidigera* contains about 10% to 12% of saponins.

In some embodiments, the *Yucca schidigera* extract can be rich in natural saponins that disrupt plaque formation. In some embodiments, the *Yucca schidigera* extract can target plaque formed in spaces between teeth, supragingival to the gumline, subgingival to the gumline, on top of chewing surfaces, such as for example, the top of molars and premolars, and the back surfaces of teeth.

In some embodiments, the *Yucca schidigera* extract can create a shield that helps prevent bacterial recolonization. In some embodiments, to combat the accumulation of harmful bacteria, the *Yucca schidigera* extract can create an unfavorable environment for harmful bacteria. In some embodiments, the *Yucca schidigera* extract can be known for anti-inflammatory properties, which help support gum health.

In some embodiments, the *Yucca schidigera* extract can be present in an amount to form a film on at least one tooth surface. In some embodiments, *Yucca schidigera* extract can be present in an amount to form a film on the gums. In some embodiments, the film can be a protective barrier on the tooth surfaces and the gums. In some embodiments, the film can be a microscopic film coating on teeth and gums.

In some embodiments, the composition comprises about 1% to 15% of the *Yucca schidigera* extract based on a total weight of the composition, or any range or subrange between 1% and 15%. For example, in some embodiments, the composition comprises about 3% to 13%, 5% to 11%, 7% to 9%, 1% to 13%, 1% to 11%, 1% to 9%, 1% to 7%, 1% to 5%, 1% to 3%, 3% to 15%, 5% to 15%, 7% to 15%, 9% to 15%, 11% to 15%, or 13% to 15% of the *Yucca schidigera* extract based on a total weight of the composition.

In some embodiments, the *Yucca schidigera* extract can help protect against acid attacks from the harmful bacteria.

In some embodiments, the protective barrier formed by the natural saponins in the *Yucca schidigera* extract can provide continuous protection to the at least one tooth surface and the gums. In some embodiments, when the *Yucca schidigera* extract is present in a sufficient amount in the composition, the *Yucca schidigera* extract can continue to work between administration of the composition. In some embodiments, the protective barrier formed by the *Yucca schidigera* extract can be an advancement over traditional water additives, which typically work during direct contact with the mouth.

In some embodiments, the *Yucca schidigera* extract can provide longer-lasting protection between drinking sessions. In some embodiments, the *Yucca schidigera* extract can maintain a healthier oral environment in between administration of the composition, such as, drinking potable water comprising the composition.

In some embodiments, the *Yucca schidigera* extract can acts as a foundation for other active ingredients to work more effectively. For example, in some embodiments, the natural saponins create an initial protective barrier that enhances the effectiveness of active ingredients, glucose oxidase and propolis extract.

In some embodiments, the *Yucca schidigera* extract can enhance the effectiveness of the active ingredients and at least one supporting ingredient by helping the least one active ingredients and at least one supporting ingredient adhere to oral surfaces longer. For example, in some embodiments, the natural saponins can help the active ingredients adhere to oral surfaces longer while supporting their antimicrobial actions through complementary mechanisms.

In some embodiments, the *Yucca schidigera* can provide relief to the companion pets' overall health. In some embodiments, the *Yucca schidigera* extract can supports digestive health. In some embodiments, the *Yucca schidigera* extract can reduce fecal odor through ammonia binding. In some embodiments, the *Yucca schidigera* extract can reduce joint inflammation. In some embodiments, the *Yucca schidigera* extract can enhances nutrient absorption.

In some embodiments, the composition can comprise a propolis extract. The propolis extract can be hard. The propolis extract can be soft. In some embodiments, the propolis extract can be collected from beehives made from bees.

In some embodiments, the propolis extract can provide powerful natural antimicrobial properties. In some embodiments, the propolis extract can contain compounds having antimicrobial properties such as, flavonoid compounds and phenolic compounds that inhibit bacterial growth. In some embodiments, the flavonoid compounds and phenolic compounds are naturally present and concentrated in propolis extract. In some embodiments, the flavonoids compounds and phenolic compounds can be antioxidants. In some embodiments, the flavonoids compounds and phenolic compounds can protect oral tissue from oxidative stress. In some embodiments, the oral tissues can comprise at least one of the gingiva (gums), oral mucosa, the tongue, the salivary glands, or any combination thereof. In some embodiments, the flavonoids compounds and phenolic compounds can support overall oral health. In some embodiments, the flavonoids compounds and phenolic compounds can work synergistically with other protective mechanisms in the composition.

In some embodiments, the propolis extract can be effective against various oral pathogens, such as *Streptococcus mutans, Porphyromona gingivalis*, and *Fusobacterium nucleatum*. In some embodiments, the propolis extract works through multiple mechanisms to disrupt bacterial cell walls.

In some embodiments, the propolis extract can be present in amount to form a coating at least one oral tissue. In some embodiments, the propolis extract can comprise natural resins to adhere to oral surfaces. In some embodiments, the oral surfaces can comprise at least one of at least one teeth, a gingival surface, a mucosal surface, a tongue surface, or any combination thereof. In some embodiments, the protective coating prevents bacterial adhesion. In some embodiments, the protective coating can form a physical barrier that helps protect the teeth and gums. In some embodiments, the propolis extract works synergistically with the *Yucca schidigera* extract protective barrier properties.

In some embodiments, the propolis extract can support gum health. In some embodiments, the propolis extract maintains healthy gum tissue. In some embodiments, the propolis extract comprises caffeic acid phenethyl ester (CAPE) and other compounds with anti-inflammatory properties.

In some embodiments, the propolis extract can aid in tissue repair. In some embodiments, the propolis extract supports natural healing processes of the gums. In some embodiments, the propolis extract can comprise compounds that promote tissue regeneration. The propolis extract can maintain healthy oral tissues.

In some embodiments, the propolis extract can support immune system function. The CAPE and other compounds can modulate immune response. In some embodiments, the flavonoids can enhance natural immune defenses, such as the production of saliva and gingival crevicular fluids. In some embodiments, the propolis extract can activate and regulate immune cells.

In some embodiments, the propolis extract can reduce harmful bacterial populations. In some embodiments, the natural compounds in propolis extract can disrupt bacterial biofilms. In some embodiments, the propolis extract can prevent bacterial colonization. In some embodiments, the propolis extract can work alongside other antimicrobial ingredients to reduce harmful bacterial population. In some embodiments, the effectiveness of reducing the harmful bacterial populations can be enhanced by the synergistic action of radish root ferment filtrate.

In some embodiments, the propolis extract can provide anti-inflammatory support. In some embodiments, the flavonoid compounds and phenolic compounds work together to reduce inflammation. In some embodiments, the propolis extract can support comfort and health of at least one oral tissue. In some embodiments, the propolis extract can maintain normal gum condition. In some embodiments, the propolis extract can be synergistic with *Yucca schidigera* extract anti-inflammatory properties.

In some embodiments, the propolis extract can have synergistic action with *Yucca schidigera* extract and glucose oxidase. In some embodiments, the propolis extract can comprise natural resins that enhance the protective barrier initiated by the *Yucca schidigera* extract. In some embodiments, the bee polis antimicrobial compounds such as, flavonoid compounds and phenolic compounds can have synergistic action with hydrogen peroxide generated by glucose oxidase to create a comprehensive approach to oral health.

In some embodiments, the composition comprises about 1% to 10% of the propolis extract based on a total weight of the composition, or any range or subrange between 1% and 10%. For example, in some embodiments, the composition comprises about 3% to 8%, 5% to 6%, 1% to 8%, 1% to 6%, 1% to 4%, 1% to 2%, 3% to 10%, 5% to 10%, 7% to 10%, and 9% to 10% of the propolis extract based on a total weight of the composition.

In some embodiments, the composition can comprise a glucose oxidase. In some embodiments, the glucose oxidase can be an enzymatic powerhouse, creating a cascade of benefits that amplify the effectiveness of the active ingredients and the at least one supporting ingredient.

In some embodiments, the glucose oxidase can be present in a sufficient amount, so when digested by a dog, the glucose oxidase generates a plurality of hydrogen peroxide molecules to enhance antimicrobial anti-inflammatory properties of the active ingredients. In some embodiments, the glucose oxidase can enzymatically generate the hydrogen peroxide through a natural chemical reaction. In some embodiments, the glucose oxidase catalyzes the reaction of glucose and oxygen to produce gluconic acid and hydrogen peroxide in low level amounts. In some embodiments, the reaction occurs continuously when glucose is present in the mouth. In some embodiments, the resulting hydrogen peroxide provides natural antimicrobial action.

In some embodiments, the glucose oxidase can be an enzyme commonly derived from the fungus *Aspergillus niger*. In some embodiments, glucose oxidase has the following chemical properties: CAS Number: 9001-37-0; Molecular Weight: Approximately 160 kDa; Isoelectric Point: 4.2; and a pH from 4 to 7.

In some embodiments, the glucose oxidase can create a protective antimicrobial environment. In some embodiments, the continuous production a plurality of hydrogen peroxide molecules are present in an amount to control bacteria growth. In some embodiments, the glucose oxidase can create an environment less favorable for pathogenic microorganisms, such as bacteria including the *Streptococcus mutans*, the *Porphyromonas gingivalis*, and *Fusobacterium nucleatum* when glucose and oxygen is present. In some embodiments, the glucose oxidase can work synergistically with the active ingredients and at least one supporting ingredient to maintain oral health.

In some embodiments, the glucose oxidase can break down food particles through enzymatic action. In some embodiments, the glucose oxidase, as an enzyme, can catalyze the breakdown of glucose molecules. In some embodiments, the breakdown of the glucose molecules can reduce available food sources for harmful bacteria. In some embodiments, the breakdown of sugars reduce the substrate for bacteria. In some embodiments, the glucose oxidase provides oral cleanliness.

In some embodiments, the glucose oxidase can support natural oral chemistry. In some embodiments, the production of gluconic acid can maintain a slightly acidic environment. In some embodiments, the pH level of the mouth can optimize the effectiveness of the active ingredients. In some embodiments, the optimal pH level of a dog's mouth is 7.0.

In some embodiments, the glucose oxidase works synergistically with natural oral enzymes present in saliva. In some embodiments, the glucose oxidase enhance saliva's natural protective properties. In some embodiments, the glucose oxidase supplements the natural enzyme systems present in saliva. In some embodiments, the glucose oxidase works synergistically existing oral defense mechanisms.

In some embodiments, the glucose oxidase and the propolis extract can adhere to the film.

In some embodiments, the composition comprises about 0.1% to 5% by weight of the glucose oxidase based on a total weight of the composition, or any range or subrange between 0.1% and 5%. For example, in some embodiments, the composition comprises about 1% to 4%, 2% to 3%, 0.1% to 4%, 0.1% to 3%, 0.1% to 2%, 0.1% to 1%, 1% to 5%, 2% to 5%, 3% to 5%, or 4% to 5% by weight of the glucose oxidase based on a total weight of the composition.

In some embodiments, the composition can comprise at least one supporting ingredient. In some embodiments, the at least one supporting ingredient can be present in a sufficient amount, so when digested by a dog, the at least one supporting ingredient maintains a potency of the active ingredients.

In some embodiments, the effectiveness the active ingredients comprising the *Yucca schidigera* extract, the glucose oxidase, and the propolis extract can work synergistically with at least one supporting ingredient. In some embodiments, each of the at least one supporting ingredient play multiple crucial roles in the composition's stability, effectiveness, and usability. In some embodiments, the at least one supporting ingredient can be present in an amount to enhance an effectiveness of the active ingredients to provide for comprehensive oral health.

In some embodiments, the at least one supporting ingredient comprises radish root ferment filtrate. In some embodiments, radish root ferment filtrate can be a natural preservative created through the fermentation of radish root by beneficial bacteria. In some embodiments, the radish root ferment filtrate can comprise antimicrobial peptides produced during fermentation. In some embodiments, the radish root ferment filtrate creates a broad-spectrum antimicrobial environment. In some embodiments, the radish root ferment filtrate can work through multiple preservation pathways. In some embodiments, the radish root ferment filtrate maintains effectiveness across the composition's pH range.

In some embodiments, radish root ferment filtrate can work with both water-soluble (hydrophilic) ingredients and oil-soluble (lipophilic) ingredients to enhance the composition stability. In some embodiments, the radish root ferment filtrate can be present in an amount to maintain a concentration of the active ingredients.

In some embodiments, radish root ferment filtrate can work synergistically with propolis extract. In some embodiments, the radish root ferment filtrate can have complementary antimicrobial mechanisms with the propolis extract to enhance overall effectiveness of the composition.

In some embodiments, the composition comprises about 0.1% to 5% of the radish root ferment filtrate based on a total weight of the composition, or any range or subrange between 0.1% and 5%. For example, in some embodiments, the composition comprises about 1% to 4%, 2% to 3%, 0.1% to 4%, 0.1% to 3%, 0.1% to 2%, 0.1% to 1%, 1% to 5%, 2% to 5%, 3% to 5%, or 4% to 5% by weight of the radish root ferment filtrate based on a total weight of the composition.

In some embodiments, the at least one supporting ingredient comprises at least one of a Vitamin C, a citric acid, a potassium sorbate, a distilled water, or any combination thereof. In some embodiments, the at least one supporting ingredient comprises at least one of a Vitamin C, a citric acid, a potassium sorbate, a distilled water, or any combination thereof can have multiple roles in maintaining the composition's stability and effectiveness. In some embodiments, the at least one supporting ingredient comprises at least one of a Vitamin C, a citric acid, a potassium sorbate, a distilled water, or any combination thereof work together to maintain optimal pH, prevent degradation, and ensure consistent performance throughout the product's shelf life.

In some embodiments, the at least one supporting ingredient can comprise Vitamin C. The Vitamin C can be an antioxidant preservative. In some embodiments, the Vitamin C can protect the composition from oxidation. In some embodiments, the Vitamin C can maintain the stability of the active ingredients and the at least one supporting ingredient. In some embodiments, the Vitamin C extends the shelf life of the composition naturally. In some embodiments, the Vitamin C works synergistically with other preservatives.

In some embodiments, the Vitamin C supports the pH balance of the composition. In some embodiments, the Vitamin C can maintain an optimal acidic environment. In some embodiments, the Vitamin C enhances the effectiveness of the preservation system. In some embodiments, the Vitamin C enhances the stability of the composition. In some embodiments, the Vitamin C enhances the performance of the active ingredients.

In some embodiments, the Vitamin C can contribute to oral health. In some embodiments, Vitamin C can be essential for collagen synthesis. Vitamin C can support gum tissue health. In some embodiments, Vitamin C can provide antioxidant protection in an oral environment. In some embodiments, Vitamin C enhances the oral tissue repair processes.

In some embodiments, the at least one supporting ingredient can comprise citric acid.

In some embodiments, the at least one supporting ingredient can maintain optimal pH balance. In some embodiments, the citric acid can function to achieve and maintain target pH range. In some embodiments, the citric acid can enhance preservative effectiveness. In some embodiments, the citric acid can support the stability of the active ingredients and the at least on supporting ingredient. In some embodiments, the citric acid can maintain antimicrobial effectiveness.

In some embodiments, the citric acid can be a chelating agent. In some embodiments, the citric acid can bind to metal ions that could destabilize the composition. In some embodiments, the citric acid can prevent the degradation of the active ingredients and the at least on supporting ingredient. In some embodiments, the citric acid can enhance the stability of the composition.

In some embodiments, the at least one supporting ingredient can comprise potassium sorbate. In some embodiments, the potassium sorbate can provide targeted preservation of the composition. In some embodiments, the potassium sorbate can be effective against yeasts and molds. In some embodiments, potassium sorbate can function effectively in the pH range of the composition. In some embodiments, potassium sorbate can enhance the stability of the composition. In some embodiments, the potassium sorbate works synergistically with the radish root ferment filtrate.

In some embodiments, the at least one supporting ingredient can comprise distilled water. In some embodiments, the use of distilled water as a base can provide a base free from mineral contaminants that can interfere with the active ingredients. In some embodiments, the distilled water can prevent unwanted chemical reactions. In some embodiments, the distilled water can provide stability for the composition.

In some embodiments, the distilled water can optimize the performance of the active ingredients. In some embodiments, the distilled water can enhance dissolution and mixing of the active ingredients and the at least one supporting ingredient. In some embodiments, the distill water maintains a concentration of the composition.

In some embodiments, the composition comprises about 75% to 95% of the distilled water based on a total weight of the composition. For example, in some embodiments, the composition comprises about 80% to 90%, 75% to 90%, 75% to 85%, 75% to 80%, 80% to 95%, 85% to 95%, or 90% to 90% of the distilled water based on a total weight of the composition.

In some embodiments, the base does not comprise purified water. In some embodiments, the composition does not comprise additives. In some embodiments, the composition can comprise the active ingredients and at least one supporting ingredient that actively contributes to at least dental health, stability of the composition, or any combination thereof.

In some embodiments, the composition can be a water additive.

In some embodiments, the composition can be unflavored. In some embodiments, the composition can be unflavored to appeal to sensitive palates.

In some embodiments, the composition can be plant-based.

In some embodiments, the composition can be a concentrated composition. In some embodiments, the composition has a greater concentration compared to traditional compositions. The concentration of the composition can permit customized dosing for different weights, animals, and sensitivities.

At step 104, in some embodiments, the method comprises administering to a dog between about 1 to 20 drops of the composition to a tap water to improve a saliva score by at least 50% as detected by Active Matrix Metalloproteinase-8 (aMMP-8), or any range or subrange between 1 and 20. In some embodiments, the administering to a dog comprises pouring between about 1 to 20 drops of the composition to a tap water to improve a saliva score by at least 50% as detected by aMMP-8. In some embodiments, the administering to a dog comprises scooping between about 1 to 20 drops of the composition to a tap water to improve a saliva score by at least 50% as detected by aMMP-8. In some embodiments, the administering to a dog comprises dispensing between about 1 to 20 drops of the composition to a tap water to improve a saliva score by at least 50% as detected by aMMP-8. In some embodiments, the administering to a dog comprises injecting between about 1 to 20 drops of the composition to a tap water to improve a saliva score by at least 50% as detected by aMMP-8. In some embodiments, the administering to a dog comprises supplying between about 1 to 20 drops of the composition to a tap water to improve a saliva score by at least 50% as detected by aMMP-8. In some embodiments, the administering to a dog comprises distributing between about 1 to 20 drops of the composition to a tap water to improve a saliva score by at least 50% as detected by aMMP-8.

In some embodiments, the method comprises administering to a dog between about 2 to 19, 3 to 18, 4 to 17, 5 to 16, 6 to 15, 7 to 14, 8 to 13, 9 to 12, or 10 to 11 drops of the composition to a tap water to improve a saliva score by at least 50% as detected by aMMP-8. In some embodiments, the method comprises administering to a dog between 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, or 19 to 20 drops of the composition to a tap water to improve a saliva score by at least 50% as detected by aMMP-8. In some embodiments, the method comprises administering to a dog between 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, or 1 to 2 drops of the composition to a tap water to improve a saliva score by at least 50% as detected by aMMP-8.

In some embodiments, a size of a drop is about 0.05 milliliters (mL).

In some embodiments, about 10 to 12 drops of the composition can be added to 24 ounces of tap water. In some embodiments, about 1 drop of the composition can be added to about 2 ounces of tap water.

In some embodiments, the tap water comprises at least one of a bottled water, a facet water, a purified water, a rainwater, or any combination thereof.

In some embodiments, with continued use of the composition, the dog's saliva score improves by at least 50%. For example, in some embodiments, with continued use of the composition, the dog's saliva score improves by at least 55%, at least 60%, at least 65%, at least 70%, at least 75%, at least 80%, at least 85%, at least 90%, at least 95%, or 100%.

In some embodiments, with continued use of the composition, the dog's saliva score comprises about 0.01 ng/mL to 30 ng/mL, or any range or subrange between 0.01 ng/ml to 30 ng/ml. For example, in some embodiments, with continued use of the composition, the dog's saliva score comprises about 0.1 ng/ml to 25 ng/mL, 1 ng/mL to 20 ng/ml, 5 ng/mL to 15 ng/mL, 0.1 ng/ml to 30 ng/mL, 1 ng/ml to 30 ng/mL, 5 ng/ml to 30 ng/mL, 10 ng/ml to 30 ng/mL, 15 ng/ml to 30 ng/mL, 20 ng/ml to 30 ng/mL, 25 ng/ml to 30 ng/mL, 0.01 ng/ml to 25 ng/mL, 0.01 ng/ml to 20 ng/mL, 0.01 ng/ml to 15 ng/mL, 0.01 ng/ml to 10 ng/mL, or 0.01 ng/ml to 5 ng/mL.

In some embodiments, a saliva score greater than 30 ng/mL can indicate poor oral health.

In some embodiments, the presence of aMMP-8 at high levels can indicate inflammation and potential periodontal disease.

In some embodiments, the composition can be administered at least once per day; once every other day; once every three days; and once per week. In some embodiments, the administration of the composition can be more than once per day.

In some embodiments, the composition can work independent of the tap water pH. In some embodiments, the composition can be effective across all pH's of tap water.

Some embodiments relate to a kit. The kit can comprise a composition and a storage container.

The kit can comprise a composition. The composition can comprise the *Yucca schidigera* extract, the propolis extract, the glucose oxidase, and the radish root ferment filtrate as described herein. In some embodiments, at least one of the propolis extract, the glucose oxidase, or any combination thereof is light sensitive. In some embodiments, the composition can comprise at least one of a vitamin C, a citric acid, a potassium sorbate, a distilled water, or any combination thereof.

In some embodiments, the kit can comprise a storage container. In some embodiments, the storage container contains the composition to stabilize at least one of the active ingredients and the at least one supporting ingredient, or any combination thereof. In some embodiments, the storage container provides a light barrier to the at least one of the active ingredients and the at least one supporting ingredient, or any combination thereof.

11

In some embodiments, the storage container can comprise an amber glass. In some embodiments, the amber glass is a primary protection to the composition. In some embodiments, the amber glass maintains the stability of the composition. The amber glass can filter out harmful UV and visible light wavelengths. In some embodiments, the harmful UV and visible light wavelengths can disrupt the stability of the composition, if exposed to the composition for an extended period of time.

In some embodiments, the storage container can comprise a label. In some embodiments, the label is a secondary protection to the composition. In some embodiments, the label is a redundant protection. In some embodiments, the label can cover at least 50% of the storage container. In some embodiments, the label covers about 50% to 99% of the storage container, or any range or subrange between 50% and 99%. For example, in some embodiments, the label covers about 60% to 90%, 70% to 80%, 50% to 90%, 50% to 80%, 50% to 70%, 50% to 60%, 60% to 99%, 70% to 99%, 80% to 99%, or 90% to 99% of the storage container.

In some embodiments, the amber glass and the label can provide a dual-layer light protection to the composition. In some embodiments, the amber glass provides a first layer light protection to the composition. In some embodiments, the label provides a second layer light protection to the composition.

Any one or more of the embodiments disclosed herein shall be understood to be combinable without departing from the scope or spirit of the disclosure.

EXAMPLE

Figure 2A:
FIG. 2A is a schematic diagram of a dog's teeth before drinking the composition, according to some embodiments.
Figure 2B:
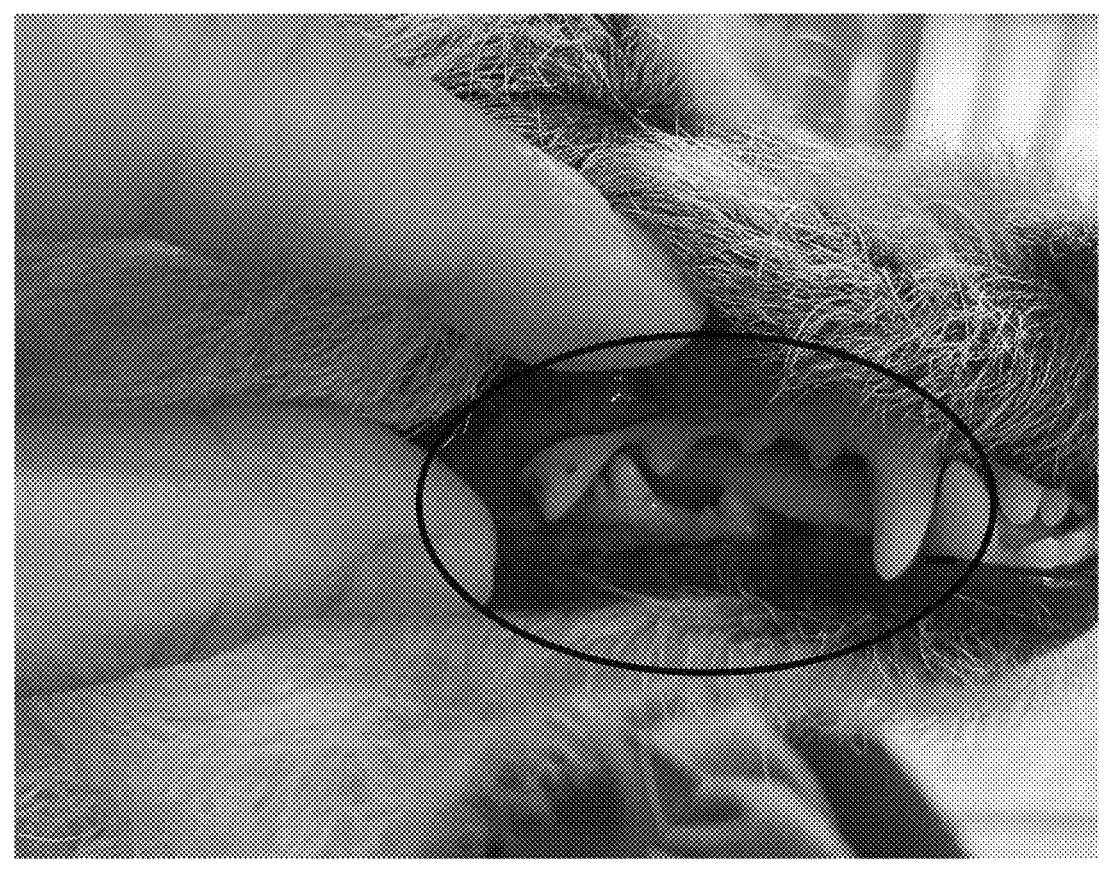
FIG. 2B is a schematic diagram of a dog's teeth at Day 26 after drinking the composition, according to some embodiments.
Figure 2C:
FIG. 2C is a schematic diagram of a dog's teeth at Day 60 after drinking the composition, according to some embodiments.

A dog was provided the composition disclosed herein. As shown in FIG. 2A, the dog was photographed to have tartar and other dental related issues. The dog owner provided the dog with the composition as an additive to the dog's daily bowl of water. The dog owner added about 10 to 12 drops of the composition to the dog's bowl of water, about 24 ounces of water. The dog owner did not brush the dog's teeth and did not provide the dog with additional dog dental treatments, such as tartar reducing chews. As shown, in FIG. 2B, at Day 26, the dog's teeth were observed to have additional reduced tartar. The dog owner continued to provide the dog the composition as an additive to the dog's daily bowl of water. The dog owner did not brush the dog's teeth and did not provide the dog with additional dog dental treatments, such as tartar reducing chews for 60 days. As shown in FIG. 2C, at Day 60, the dog teeth is observed to have reduced tartar and dental related issues.

ASPECTS

Various Aspects are described below. It is to be understood that any one or more of the features recited in the following Aspect(s) can be combined with any one or more other Aspect(s).

---

Aspect 1.

---

A method of treating dog dental health comprising:
obtaining a composition comprising:
  active ingredients,
    wherein the active ingredients comprises:
      a yucca schidigera extract,
      a propolis extract, and
      a glucose oxidase,
        wherein the glucose oxidase is present in a

12

-continued

---

Aspect 1.

--- sufficient amount, so when digested by a dog,
  generates a plurality of hydrogen peroxide
  molecules to enhance antimicrobial anti-
  inflammatory properties of the active ingredients;
at least one supporting ingredient,
  wherein the at least one supporting ingredient comprises:
    a radish root ferment filtrate;
  wherein the at least one supporting ingredient is present in a
  sufficient amount, so when digested by a dog, the at least one
  supporting ingredient maintains a potency of the active
  ingredients; and
administering to a dog between about 1 drop to 20 drops of the
composition to a tap water to improve a saliva score by at least 50% as
detected by Active Matrix Metalloproteinase-8 (aMMP-8).

---

Aspect 2. The method according to Aspect 1, wherein the at least one supporting ingredient further comprises at least one of a vitamin C, a citric acid, a potassium sorbate, a distilled water, or any combination thereof.

Aspect 3. The method according to any one of Aspects 1-2, wherein the composition comprises about 1% to 15% of the *Yucca schidigera* extract based on a total weight of the composition.

Aspect 4. The method according to any one of Aspects 1-3, wherein the composition comprises about 75% to 95% of the distilled water based on a total weight of the composition.

Aspect 5. The method according to any one of Aspects 1-4, wherein the composition comprises about 1% to 10% of the propolis extract based on a total weight of the composition.

Aspect 6. The method according to any one of Aspects 1-5, wherein the composition comprises about 0.1% to 5% of the radish root ferment filtrate based on a total weight of the composition.

Aspect 7. The method according to any one of Aspects 1-6, wherein the composition comprises about 0.1% to 5% of the glucose oxidase based on a total weight of the composition.

Aspect 8. The method according to any one of Aspects 1-7, wherein the composition comprises about 0.1% to 5% by weight of the glucose oxidase based on a total weight of the composition.

Aspect 9. The method according to any one of Aspects 1-8, wherein about 1 drop of the composition is administered to about 1 ounce 3 ounces of the tap water.

Aspect 10. The method according to any one of Aspects 1-9, the *Yucca schidigera* extract is present in a sufficient amount to form a film on at least one tooth surface.

Aspect 11. The method according to any one of Aspects 1-10, wherein the composition is unflavored.

Aspect 12. The method according to any one of Aspects 1-11, wherein the propolis extract is present in a sufficient amount to form a coating at least one oral tissue.

Aspect 13. The method according to any one of Aspects 1-12, wherein each of the 1 drop to 20 drops comprises 0.05 milliliters (mL).

Aspect 14. The method according to any one of Aspects 1-13, the plurality of hydrogen peroxide molecules are present in a sufficient amount to control bacteria growth on an oral surface.

13

Aspect 15. A composition comprising:
active ingredients,
  wherein the active ingredients comprises:
    a *Yucca schidigera* extract,
    a propolis extract, and
    a glucose oxidase,
      wherein the glucose oxidase is present in a suffi-
      cient amount, so when digested by a dog, gener-
      ates a plurality of hydrogen peroxide molecules to
      enhance antimicrobial anti-inflammatory proper-
      ties of the active ingredients; and
  at least one supporting ingredient,
    wherein the at least one supporting ingredient com-
    prises:
      a radish root ferment filtrate;
    wherein the at least one supporting ingredient is present
      in a sufficient amount, so when digested by a dog, the
      at least one supporting ingredient maintains a
      potency of the active ingredients.
Aspect 16. The composition according to Aspect 15,
wherein the at least one supporting ingredient further com-
prises at least one of a Vitamin C, a citric acid, a potassium
sorbate, a distilled water, or any combination thereof.
Aspect 17. The composition according to any one of
Aspects 15-16, wherein the composition is a water additive.

---

Aspect 18.

A kit comprising:
a composition,
  wherein the composition comprises:
    active ingredients,
      wherein the active ingredients comprises:
        a yucca schidigera extract,
        a bee propolis, and
        a glucose oxidase,
          wherein the glucose oxidase is present in
          a sufficient amount, so when digested by
          a dog, generates a plurality of hydrogen
          peroxide molecules to enhance
          antimicrobial anti-inflammatory
          properties of the active ingredients; and
    at least one supporting ingredient,
      wherein the at least one supporting ingredient
      comprises:
        a radish root ferment filtrate;
      wherein the at least one supporting ingredient is
      present in a sufficient amount, so when digested by a
      dog, the at least one supporting maintains a potency of
      the active ingredients; and
a storage container,
  wherein the storage container comprises:
    an amber glass, and
    a label,
      wherein the label covers at least 50% of the storage
      container; and
  wherein the storage container contains the composition to stabilize
  the at least one of the active ingredients and the at least one
  supporting ingredient, or any combination thereof;
  wherein the storage container provides a light barrier to the
  composition.

---

Aspect 19. The kit according to Aspect 18, wherein the
amber glass and the label provide a dual-layer light protec-
tion to the composition.
Aspect 20. The kit according to any one of Aspects 18-19,
wherein at least one of the propolis extract, the glucose
oxidase, or any combination thereof is light sensitive.

14

What is claimed is:
1. A method of treating dog dental health comprising:
  obtaining a liquid water additive composition comprising:
    active ingredients,
      wherein the active ingredients comprise:
        a *Yucca schidigera* extract,
        a propolis extract, and
        a glucose oxidase,
          wherein the glucose oxidase is present in a
          sufficient amount, so when digested by a dog,
          generates a plurality of hydrogen peroxide mol-
          ecules to enhance antimicrobial anti-inflamma-
          tory properties of the active ingredients;
      at least one supporting ingredient;
        wherein the at least one supporting ingredient com-
        prises:
          a radish root ferment filtrate;
        and
  adding about 1 drop to 20 drops of the liquid water
    additive composition to a dog's drinking water to result
    in a dental composition;
  administering the dental composition to the dog; and
  preparing additional dental compositions and administer-
    ing these additional dental compositions to the dog for
    a sufficient amount of time to reduce tartar buildup.
2. The method of claim 1, wherein the at least one
supporting ingredient further comprises at least one of a
vitamin C, a citric acid, a potassium sorbate, a distilled
water, or any combination thereof.
3. The method of claim 1, wherein the composition
comprises about 1% to 15% of the *Yucca schidigera* extract
based on a total weight of the composition.
4. The method of claim 2, wherein the composition
comprises about 75% to 95% of the distilled water based on
a total weight of the composition.
5. The method of claim 1, wherein the composition
comprises about 1% to 10% of the propolis extract based on
a total weight of the composition.
6. The method of claim 1, wherein the composition
comprises about 0.1% to 5% of the radish root ferment
filtrate based on a total weight of the composition.
7. The method of claim 1, wherein the *Yucca schidigera*
extract comprises about 10% to 2% of saponins.
8. The method of claim 1, wherein the composition
comprises about 0.1% to 5% by weight of the glucose
oxidase based on a total weight of the composition.
9. The method of claim 1, wherein about 1 drop of the
composition is added to about 1 ounce to about 3 ounces of
the dog's drinking water.
10. The method of claim 1, the *Yucca schidigera* extract
is present in a sufficient amount to form a film on at least one
tooth surface.
11. The method of claim 1, wherein the composition is
unflavored.
12. The method of claim 1, wherein the propolis extract
is present in a sufficient amount to form a coating at least one
oral tissue.
13. The method of claim 1, wherein each of the 1 drop to
20 drops comprises 0.05 milliliters (ml).
14. The method of claim 1, wherein the plurality of
hydrogen peroxide molecules generated by the composition
after digestion by the dog are present in a sufficient amount
to control bacteria growth on an oral surface.

* * * * *